United States Patent [19]

Mhatre et al.

[11] 4,188,577
[45] Feb. 12, 1980

[54] PULSE EDDY CURRENT TESTING APPARATUS FOR MAGNETIC MATERIALS, PARTICULARLY TUBES

[75] Inventors: Girish P. Mhatre, Yonkers; Robert A. Brooks, Rye, both of N.Y.

[73] Assignee: Magnetic Analysis Corporation, Mount Vernon, N.Y.

[21] Appl. No.: 749,702

[22] Filed: Dec. 10, 1976

Related U.S. Application Data

[63] Continuation-in-part of Ser. No. 639,796, Dec. 11, 1975, abandoned.

[51] Int. Cl.² ............................................. G01N 27/86
[52] U.S. Cl. ................................. 324/220; 324/233; 324/232; 324/238
[58] Field of Search ................... 324/37, 40, 220, 232, 324/233, 238, 240–242

[56] References Cited

U.S. PATENT DOCUMENTS

| | | | |
|---|---|---|---|
| 2,258,837 | 10/1941 | Zuschlag | 324/37 |
| 2,511,568 | 6/1950 | Callan | 324/34 |
| 2,965,840 | 12/1960 | Renhen et al. | 324/37 |
| 3,235,795 | 2/1966 | Uozumi | 324/40 |
| 3,302,105 | 1/1967 | Libby et al. | 324/40 |
| 3,340,466 | 9/1967 | Ono | 324/40 |
| 3,526,829 | 9/1970 | Noble | 324/40 |
| 3,786,347 | 1/1974 | Mansson | 324/40 |
| 3,798,538 | 3/1974 | Mansson | 324/233 |
| 3,798,539 | 3/1974 | Brooks et al. | 324/40 |
| 3,809,998 | 5/1974 | Mansson | 324/40 X |
| 3,848,182 | 11/1974 | Gerner et al. | 324/233 |
| 3,852,663 | 12/1974 | Brooks | 324/40 |
| 3,952,315 | 4/1976 | Cecco | 324/37 |

OTHER PUBLICATIONS

Uozumi, Nondestructive Testing by the Pulsed Electromagnetic System, Proc. of the 4th Internal Conf. on N.D.T., London, Sep. 9–13, 1963, Publ. Butterworth, 1964.

*Primary Examiner*—Robert J. Corcoran
*Attorney, Agent, or Firm*—Pennie & Edmonds

[57] ABSTRACT

DC magnetizing pulses produce unidirectional flux in the object under test, advantageously into the saturation region thereof. The DC pulses have, or are accompanied by, an AC component for producing eddy currents in the object, and variations in the eddy currents are sensed and used to produce corresponding signals. In a preferred embodiment composite DC pulses having a relatively broad initial value followed by shorter DC pulses are intermittently applied to a primary coil wound around the core of a probe adapted to be inserted into a tube in situ. Small null coils provide an output signal. Quadrature detection and gating means yield outputs corresponding to sufficient saturation of an object, and free from transients due to the intermittent bursts of pulses. Flaw detector and comparator type apparatus are described, including bridge configurations in which the AC component is applied to the bridge. A differentiated output of a single null coil or a comparator coil may be used to give an indication of saturation.

19 Claims, 19 Drawing Figures

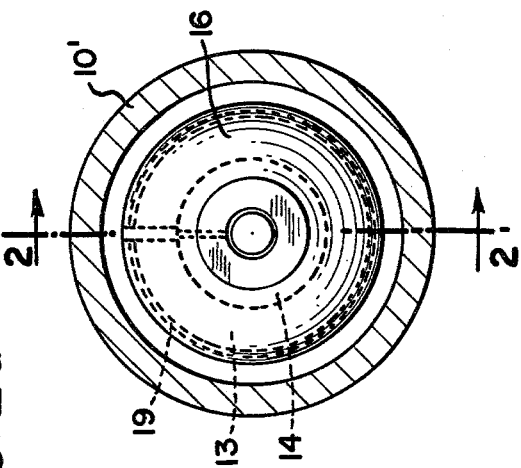
FIG. 2a
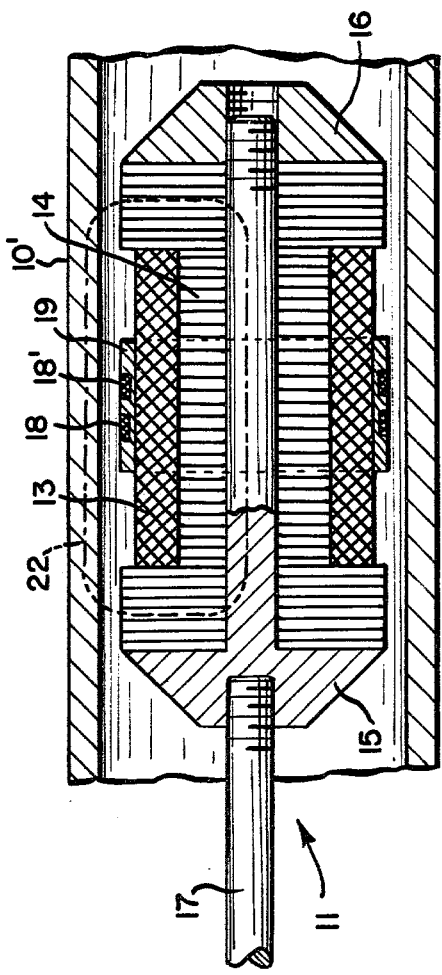
FIG. 2
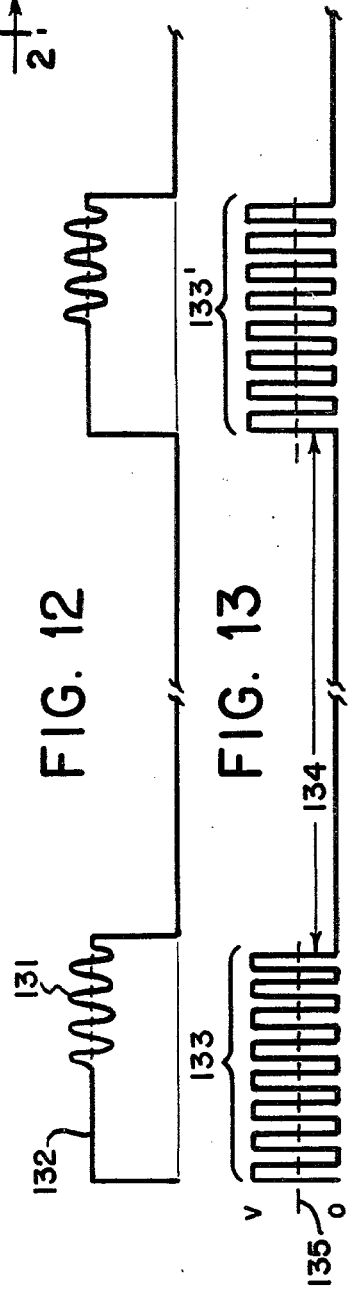
FIG. 12
FIG. 13
FIG. 14

PULSE EDDY CURRENT TESTING APPARATUS FOR MAGNETIC MATERIALS, PARTICULARLY TUBES

This application is a continuation-in-part of application Ser. No. 639,796, filed Dec. 11, 1975, for "PULSE EDDY CURRENT TESTING APPARATUS FOR MAGNETIC MATERIALS, PARTICULARLY TUBES" now abandoned.

The present invention relates to eddy current nondestructive testing of magnetic materials, especially to determine flaws and defects therein. It is particularly directed to the testing of tubes of magnetic material from the inside thereof, wherein the problems are especially severe. However, if desired, certain features of the invention may be applied to apparatus for testing tubes, coils and the like from the exterior thereof, and to comparator type apparatus.

Eddy current testing relies primarily upon conductivity variations to determine flaws and defects therein, or in general any changes which alter the eddy current flow. For simplicity, hereinafter the term "flaws" will be used to cover similar defects or variations. Eddy currents are induced in an object under test, and variations in the eddy currents are detected and indicated. In testing magnetic material, changes in permeability of the material produce a noise background which masks changes in conductivity produced by flaws, etc. Such permeability changes may be due to localized stresses and work hardening, among other factors. Although gross flaws may still be detectable, smaller flaws may remain undetected. Yet small flaws may be quite important, particularly when it is desired to determine the condition of, say, a tube, prior to actual rupture.

It has heretofore been suggested to use a DC magnetizing force to saturate magnetic material, thereby eliminating the effect of variations in permeability. Coils energized with DC current have been suggested, but are subject to overheating if made small enough to insert in a tube, particularly when sufficient current is employed for materials requiring high field strengths to saturate. Also, an additional coil is employed. Permanent magnets have also been suggested, but these are bulky and may not yield sufficient magnetizing forces.

The present invention employs DC pulses for producing magnetic flux in an object under test which reduces the permeability thereof, and preferably drives the object into its saturation region wherein its permeability is small compared to its maximum permeability. The DC pulses have, or are accompanied by, a voltage having a substantial AC component for inducing eddy currents in the object, and variations in the eddy currents are sensed and used to produce signals corresponding to flaws in the object. The frequency of the AC component is sufficiently high to secure effectivve flaw detection, and the component occurs during or immediately after the DC pulses so that flaw signals are obtained while the DC pulses are effective to reduce the permeability of the object.

Broadly, DC pulses and a voltage having a substantial AC component are applied to a test head including coil means adapted to be magnetically coupled with the object under test, and circuit means are connected with the coil means for producing a signal corresponding to variations in the eddy currents. The resulting signal is then processed to produce flaw indications.

The AC component is preferably produced by DC pulses which are short compared to the magnetizing DC pulses, so that the DC component of the short pulses contributes to the magnetizing of the object under test, or at least helps to maintain the magnetic field therein until test signals have been obtained.

Advantageously composite DC pulses are employed having a relatively broad DC component and also the AC component, the period of the AC component being short compared to the duration of the composite pulse. Preferably the composite pulses each comprise a relative broad DC pulse and a plurality of substantially shorter DC pulses. Desirably the shorter DC pulses ride on or form a part of the broad DC pulse so that their DC values contribute to the overall DC component. Several examples are given in the specific embodiments described hereinafter. The composite pulses are applied intermittently and may be widely separated in time, for example with a 12 percent duty cycle, thus greatly reducing the average heating while permitting high peak currents in the pulses.

The test head may be provided with various test coil arrangements as known in the field of eddy current testing for receiving a voltage having an AC component to produce eddy currents in the object under test and sense variations therein, with provision for receiving large DC pulses for producing unidirectional magnetic fields in the object.

In accordance with preferred arrangements of the invention, pulses having the desired DC and AC components are applied to a single driving coil of the test head, the coil being designed to withstand the necessary high current without overheating. Then pickup coil means, preferably a pair of pickup coils connected in opposition to form a null configuration, are employed to sense variations in the eddy currents. Inasmuch as the pickup coils are not required to pass heavy currents, they can be made small and short so as to facilitate detecting small flaws with adequately high sensitivity.

With such an arrangement it is possible to make a probe sufficiently small to be inserted into tubes so that they may be tested in situ. A core of magnetic material is employed so that very high magnetizing forces can be obtained. For example, magnetizing forces of 1000 oersteds and higher have been obtained in probes having diameters in the range of 0.6 to 2.25 inches. This is considered highly important, since it enables tubes to be tested without removing them from their head plates. Then, if flaws are found which are sufficiently serious to require replacement, only the tube exhibiting such flaws need be replaced. It also enables periodic tests to be made to guard against failure while in service.

In eddy current testing it is desirable to detect variations in both amplitude and phase of the eddy current signals. For example, quadrature detection may be employed to produce a pair of quadrature component signals 90° out of phase. This facilitates flaw classification and aids in determining the seriousness of the flaws. When DC pulses are applied to the test head intermittently, transients occur at the beginning of each test pulse burst, or in general at the initiation of each successive AC component. Thus detector signals produced during the initial transients will be in error. In order to obtain detected signals representing stable values, gating means are associated with the detection so that the detected signals used for subsequent processing are produced at intervals delayed with respect to the respective initiations of successive AC components. Thus the resulting detected signals are free from transient effects resulting from the intermittent application of the test signals.

With composite pulses each having a burst of short DC pulses, the intervals are advantageously at or near the end of respective bursts. In the specific embodiments described hereinafter, the outputs of the quadrature detectors are applied to respective second detectors which are gated to pass the quadrature component signals at the ends of the composite pulses.

In order to determine the current required to adequately saturate the tube or other object under test, preliminary tests may be made on a sample having an artificial flaw formed therein. Or, under test conditions, the current may be increased until the background noise is reduced to a minimum. However, it is desirable to have a continuous indication that the object under test is being driven into its saturation region. In accordance with a further feature of the invention, an output of the test head which corresponds to the build-up of unidirectional flux in the object is differentiated and indicated. During the buildup, distortion products are produced as the material is driven into the saturation region, and these distortion products are emphasized by the differentiation.

In flaw detectors as described above, both DC magnetizing pulses and AC components are applied to a single driving coil of the test head or probe. It is also possible to apply the DC magnetizing pulses to the driving or primary coil, and a test voltage having an AC component to the pair of pickup coils, for example by connecting the pickup coils in a bridge configuration with the AC component applied across one diagonal and the signal taken from the other diagonal. With quadrature detection and gating it is possible to apply test pulses (or a sinusoidal test voltage if desired) throughout the duration of the DC magnetizing pulses or even continuously, and the gating intervals delayed with respect to the respective initiations of the DC pulses and AC components occurring during or immediately after the DC pulses. In this manner the detected signals correspond to measurements made while the object is sufficiently saturated, and after any transients occurring at the beginning of a DC pulse or the beginning of an AC component having sufficiently disappeared.

Further, the DC magnetizing pulses may be used in comparator type apparatus wherein an object in a test coil head is compared with a reference object in a reference coil head, or wherein a reference signal is established with a reference object in the test coil head and used to determine variations in subsequent objects placed in the test coil head. In such cases quadrature detecting and gating are employed to develop signals at delayed intervals which correspond to sufficient saturation of objects in the test head and are stable values after transients have sufficiently disappeared.

BRIEF DESCRIPTION OF THE DRAWINGS

FIGS. 2 and 2a illustrate one embodiment of a probe assembly used in apparatus of the invention, FIG. 2 being taken along the line 2—2 of FIG. 2a;

FIG. 12 illustrates a modified composite DC pulse;

FIGS. 13 and 14 illustrate alternative pulse waveforms for testing magnetic materials.

DESCRIPTION OF THE PREFERRED EMBODIMENTS

Figure 1:
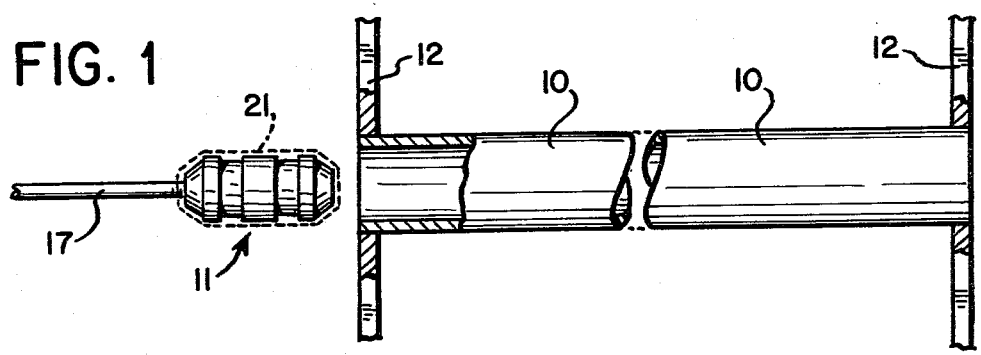
FIG. 1 illustrates internal probing of a tube.

FIG. 1 illustrates a tube 10 to be tested by an internal probe 11. The tube represents, for example, a boiler or heat exchanger tube mounted in support sheets 12. Commonly such tubes are made of magnetic material, for example, of low carbon or magnetic stainless steel, and a large number of tubes are mounted in the walls. Probe 11 is designed to be passed down the inside of a tube in situ, so that the condition of the tube may be tested without removing it.

FIGS. 2 and 2a show a suitable test probe. A primary coil 13 is wound on a laminated core 14. Desirably, a core material is chosen which saturates at a higher flux density than that required for the tubes to be tested, e.g. vanadium Permendur. A capped bolt 15, e.g. of ingot iron, with a threaded end cap 16, holds the core together. A tapped recess allows convenient attachment of a cable 17 for moving the probe through a tube under test. The primary coil 13 is encircled by a pair of null detector coils 18, 18' wound on a suitable coil form 19. The probe may be encapsulated as shown at 21 in FIG. 1 to avoid damage during use.

A section of the tube 10 to be tested is indicated at 10', and one flux path through the core and the tube wall is indicated at 22. Small air gaps will normally exist between the probe and the ID of the tube, since it is necessary to allow for the accumulation of scale, dirt, etc. in the tube. Overall, the probe is designed to produce a high flux density in the tube wall as efficiently as possible.

In one particular probe the primary consisted of about 40 turns and peak pulse currents of 100 amperes and higher were applied, thereby providing over 4000 ampere turns for producing the magnetic field. The number of ampere turns required will depend on how easy or difficult it is to saturate the material of the tube, as well as on the probe dimensions, tube wall thickness, etc. Field strengths up to 18-21 kilogausses may be required. For present applicatons a design criteria of 1000 oersteds for the magnetizing force of the probe has been employed, but this may vary considerably.

At high current levels it may be desirable to provide means for cooling the probe, such as air cooling.

Figure 3:
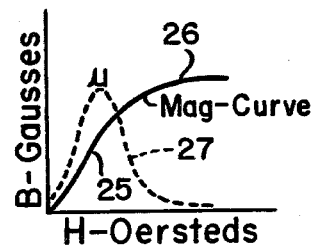
FIG. 3 shows typical normal magnetization and permeability curves of a magnetic material.

FIG. 3 illustrates a typical normal magnetization curve 25 of a magnetic material. At very low values of the magnetizing force H, the flux density B is small and curves upward. The flux density then increases markedly as the magnetizing force increases until the knee 26 of the curve is reached, whereupon the curve flattens off in the saturation region. The curve is shown as conventionally plotted with semilogarithm coordinates, so as to permit showing the high magnetization region. If plotted with linear coordinates, the knee is much sharper.

Dotted curve 27 illustrates the permeability (B/H). The permeability depends upon the flux density and is in general small at low flux densities, maximum at moderate values of flux density, and then decreases to a small value in the saturation region of the material.

When an alternating magnetizing force is superposed upon a DC magnetizing force, the permeability offered to the alternating force may be termed "incremental permeability" and may be defined as $\Delta B/\Delta H$. Inasmuch as, in eddy current testing, it is desired to avoid changes in permeability, it is desirable to have the incremental permeability approach unity. The incremental permeabiliy depends on the magnitude of the AC force, the magnitude of the DC force, and the magnetic properties of the material as well as its previous history. In general, the larger the DC magnetizing force, the smaller the incremental permeability becomes. Also, with a DC magnetizing force near the knee of the B-H curve, the smaller the AC amplitude the smaller the incremental permeability.

It is presently preferred to employ a sufficiently high DC magnetizing force to drive the material into the saturation region thereon wherein its permeability is small compared to its maximum permeability. The latter is illustrated by the peak of curve 27 in FIG. 3.

The shape of the curves shown in FIG. 3 may vary considerably depending upon the magnetic material involved, and the strength of the magnetizing force required to produce saturation may vary widely. In some cases it may be difficult to produce a sufficiently high flux density to reduce the incremental permeability to unity, without excessive heating and destruction of the probe assembly. However, by producing a flux density sufficiently high to reduce the permeability to a relatively low value, a significant increase in the sensitivity of the apparatus to small flaws may be obtained.

FIG. 4a shows a series of composite pulses for energizing the driving or primary coil of a test head probe which is presently preferred. Each composite pulse 30 comprises a broad DC pulse 31 on which is superposed a series of short DC test pulses 32 whose period is short compared to the duration of the composite pulse. After a considerable delay, the composite pulse recurs, as indicated by the interrupted line 33.

Considering first the broad pulse 31, this is a DC or unidirectional voltage pulse extending from a reference potential dented "0", usually ground potential, to a higher level V. Inasmuch as it is a DC pulse, it will produce a DC or unidirectional current in the coil, and consequently DC or unidirectional flux in the object adjacent the coil. Since the coil has inductance, the current will rise during the pulse as indicated by the dotted line 34. At the end of the pulse, the current will decay as indicated at 35. The inductance of the coil is determined in part by the magnetic material under test, and consequently the shape of the current curves will in part depend upon the material under test. Preferably the peak value and length of the pulse is selected so that the material is driven into its saturation region prior to the end of the pulse. As the permeability changes, the shape of the current waveform will also change and, when the permeability approaches unity, a break may occur with a different slope thereafter. Thus the curves 34 and 35 illustrate only the general trend.

The series of test pulses 32 permits detecting flaws in the object under saturation conditions. Their frequency (PRF) may be selected according to known principles of eddy current testing. For example, 2.5-80 kHz have been employed. Inasmuch as the pulses extend above the level of the broad pulse, they do not detract from the DC magnetization produced by the broad pulse. Indeed, since the test pulses also have a DC component determined by their duty cycle, they add somewhat to the DC magnetization. For example, 25, 50 or 75% duty cycles may be employed, yielding corresponding percentages of the DC component thereof. Other duty cycles could be employed if desired.

After an interval the composite pulse repeats, as shown at 30', so that the composite pulses are intermittently applied to the primary coil. The overall duty cycle may be chosen sufficiently low to avoid excessive heating and possible destruction of the probe. A $12\frac{1}{2}\%$ duty cycle has been employed with success, yielding an average heating current approximately $12\frac{1}{2}\%$ of the peak current.

Only four test pulses are shown in FIG. 4a, but in practice a considerably larger number may be employed. For example, in one test the duration of the composite pulse was 12.6 ms and the test pulses were a burst of 10 kHz pulses occuring during the latter half of the composite pulse. Thus, approximately 60 test pulses were present in place of the four shown. This is impractical to illustrate.

FIG. 4b shows a similar composite pulse, but the peak values of the test pulses 36 are equal to the initial value 37 of the broad pulse. The minimum values 38 of the test pulses are greater than the minimum value 39 of the composite pulse. Here the DC component of the composite pulse is slightly reduced during the latter portion thereof, by an amount depending upon the duty cycle of the test pulses, the duration of the test pulse burst, and the minimum level 38 thereof. However, in many cases this reduction may be unimportant.

FIG. 4c shows a further embodiment in which the test pulses 41 occur at the end of the broad pulse 42. The combination may be considered to be a composite pulse 43 which recurs intermittently as indicated at 43'. Although the DC component of the test pulses is lower than that of the broad pulse, satisfactory results may be obtained in many applications. The inductance of the coil to which the pulses are applied will oppose the decay of current after the end of pulse component 42, and each pulse 41 will partially restore the current. This may suffice to permit testing while the magnetic material is still in its saturation region, or at least magnetized sufficiently to reduce its permeability to an adequately low value.

In describing the waveforms, reference has been made to minimum and maximum values, etc. It will be understood that the waveforms actually applied to the coil may have the polarity shown, or the inverse thereof, and that minimum, maximum and similar values are with respect to the reference level 0 (usually ground).

Figure 4:
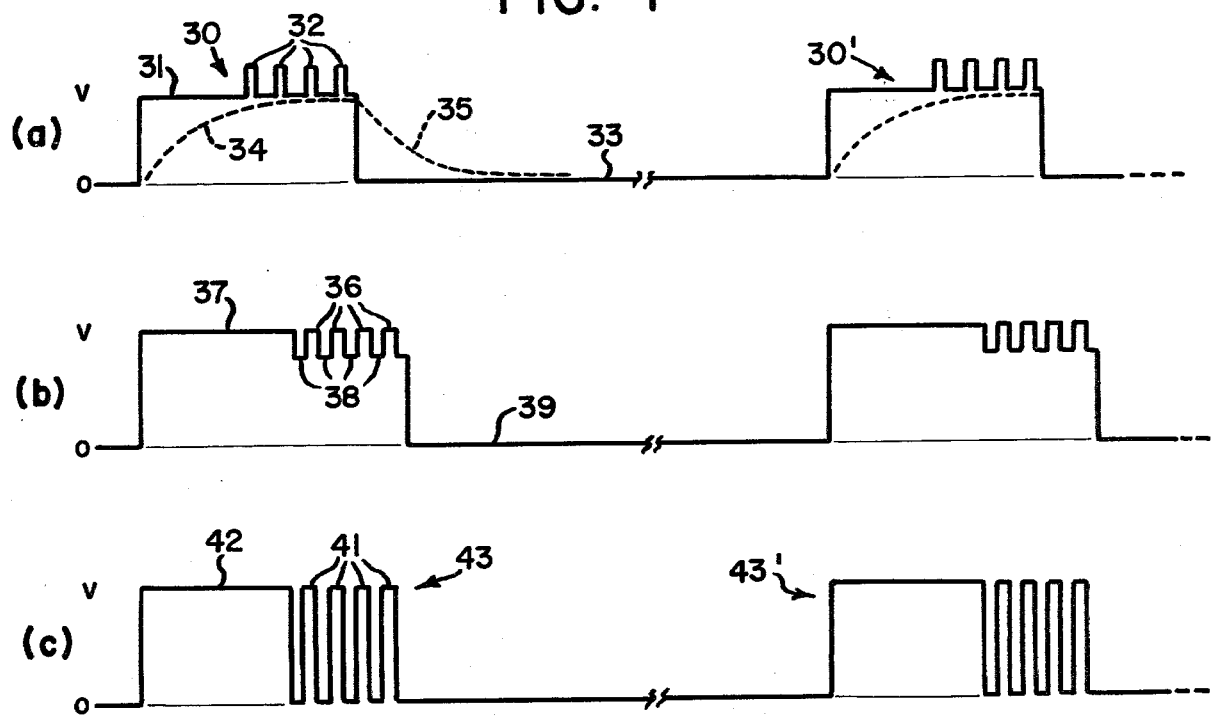
FIG. 4 illustrates composite DC pulse waveforms used in apparatus of the invention.
Figure 5:
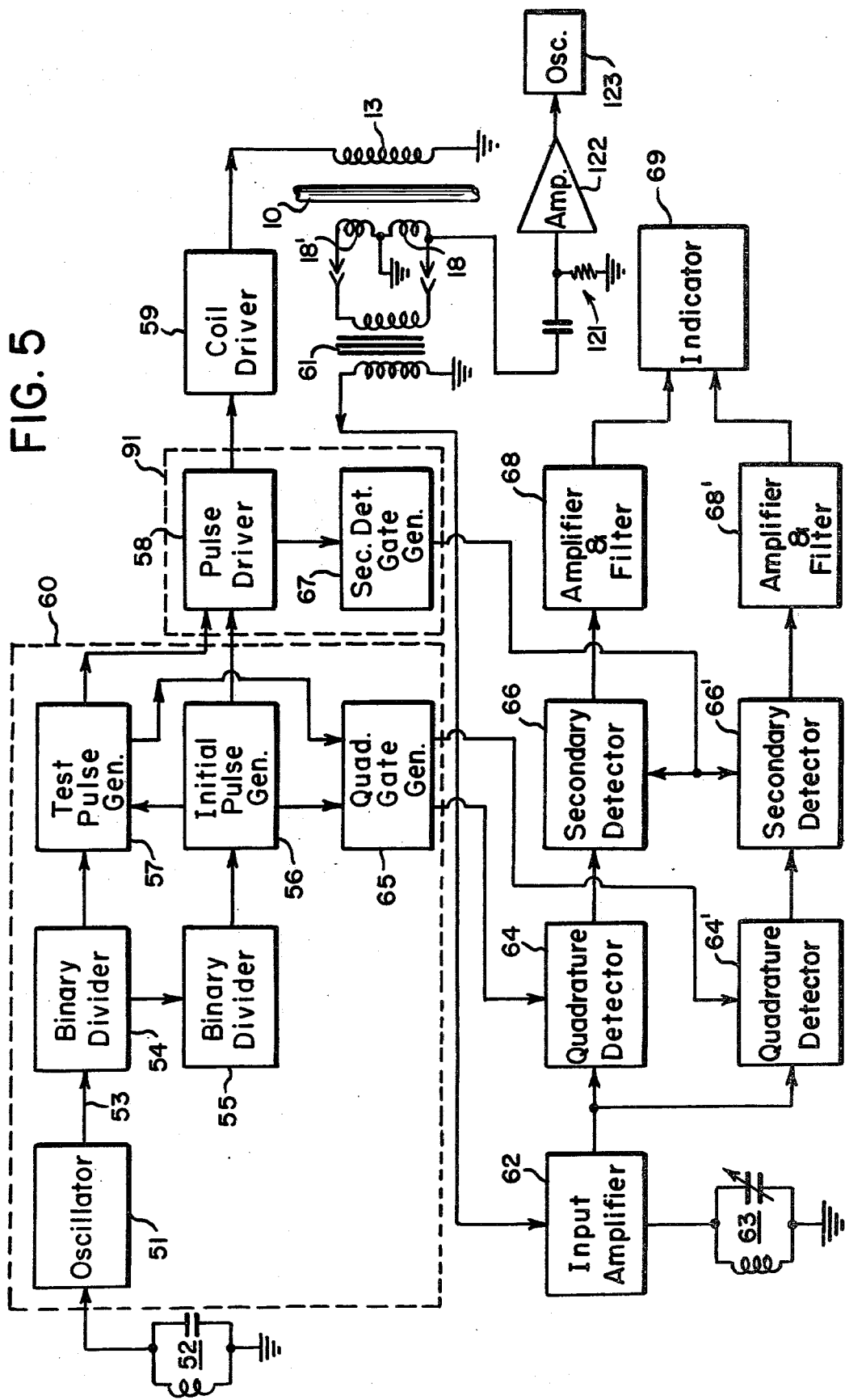
FIG. 5 is a block diagram of eddy current testing apparatus in accordance with the invention.

FIG. 5 is a block diagram of eddy current testing apparatus in accordance with the invention. An oscillator and square wave generator is shown at 51. Advantageously the oscillator may be a sine wave generator tuned by a tank circuit 52, and the sine wave squared to produce a square wave output in line 53. The square wave is then divided in 54 to produce the desired PRF for the test pulses. A selected output of 54 is supplied to a further divider 55 to produce initial broad pulses of the desired duration. The output of 55 is supplied to an initial pulse generator 56 which produces broad DC pulses of the desired duration and duty cycle. The outputs of 54 and 56 are supplied to a test pulse generator 57 which produces bursts of test pulses at the desired portion of the initial broad pulse. The outputs of 56 and 57 are then supplied to a pulse driver 58 which produces the composite pulses shown in FIG. 4a. The composite pulses are supplied to a coil driver 59 and thence to the primary driving coil 13 of the probe.

The DC component of the composite DC pulse produces magnetic flux in the wall of the tube under test, preferably sufficient to drive it into its saturation region, and the AC component produces eddy currents in the wall. Variations in the eddy currents due to flaws or other defects therein are picked up by null coils 18 and 18'. Although the primary and null coils are here shown external to tube 10, for convenience, they are actually inside the tube as illustrated in FIG. 2.

The outputs of the null coils 18, 18' are supplied through transformer 61 to an input amplifier 62. Amplifier 62 is tuned, as indicated by the tank circuit 63. Ordinarily the amplifier is tuned to the PRF of the test pulses. However, if desired for particular applications, it may be tuned to a harmonic of the PRF or to a frequency related to the pulse width as described in U.S. Pat. No. 3,786,347 to Mansson.

The output of amplifier 62 is supplied to a pair of quadrature detectors 64, 64'. Quadrature gates corresponding to the test pulse series are produced in 65 from the test pulse generator 57, and confined to the desired intervals by a signal from the initial pulse generator 56.

As will be understood from FIG. 4a, the test pulse bursts are intermittent. Consequently, at the beginning of a given burst there will be a transient condition. Also, there will be transient conditions in the tuned circuit 63 of the amplifier. In order to eliminate transient responses, and produce indicating signals only after a steady state condition has been reached, the outputs of the quadrature detectors are supplied to a pair of second detectors 66, 66'. These are gated by signals from 67 at intervals delayed with respect to the initiation of successive test pulse bursts.

In the preferred embodiment described hereinafter, the gating is at the end of the composite signal of FIG. 4a, so that a maximum time is allowed for the quadrature signals to reach steady values. This also permits changing the PRF of the test pulses, and the duration of the composite pulse, without requiring adjustment of the second detector gating. The second detectors may be of the sample-and-hold type, so that their outputs are held constant until changed by a subsequent test pulse burst. If the quadrature detectors hold their outputs at the termination of respective test pulse bursts, the second detectors may be gated after the end of a composite pulse if desired.

The resulting quadrature signals from 66, 66' are supplied to amplifiers and filters 68, 68', and then to indicator 69. They may follow conventional practice. The indicator 69 may be a cathode ray tube which displays both amplitude and phase of flaw signals. Recording, alarm circuits, etc. may be provided as desired.

Figure 6:
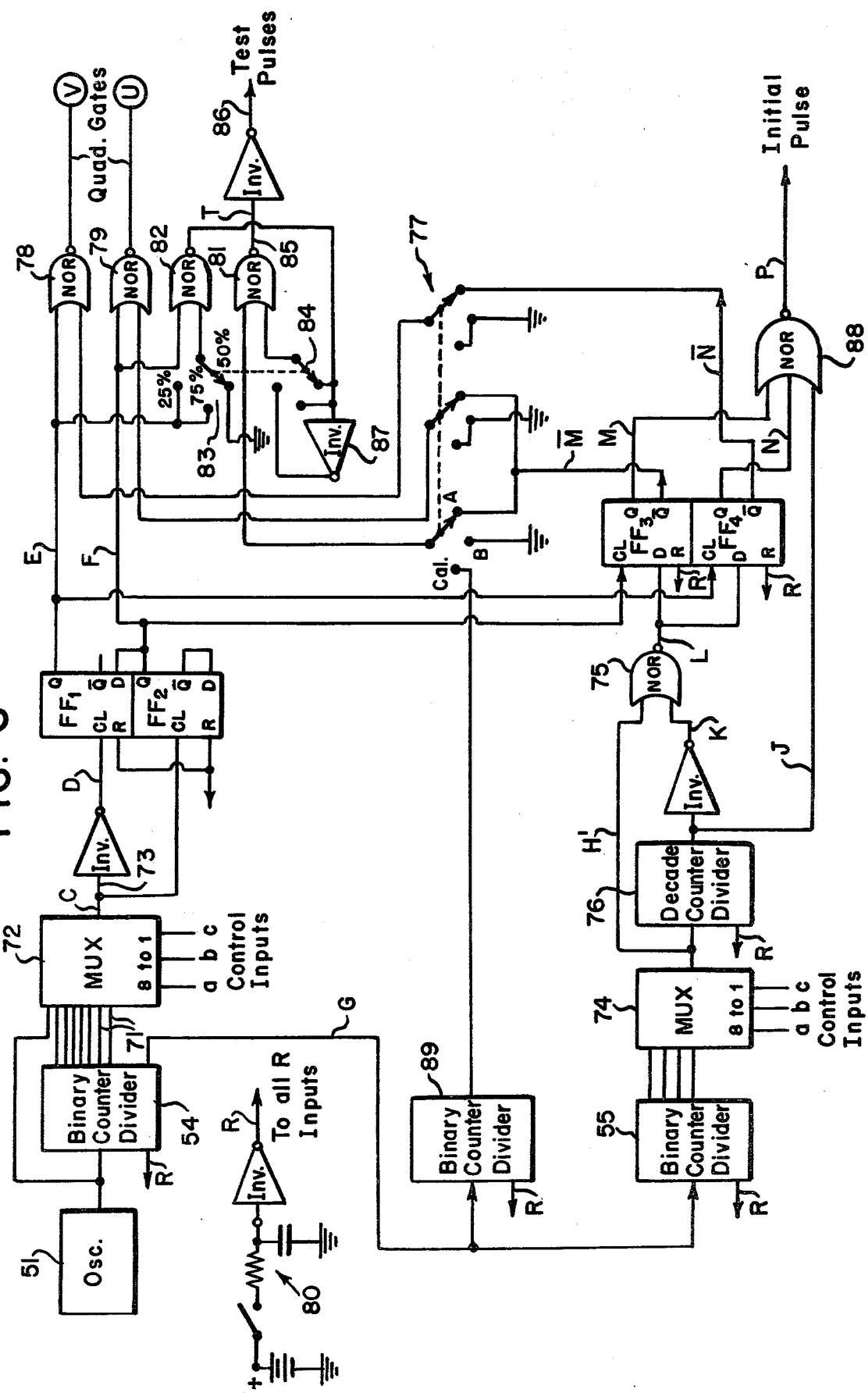
FIG. 6 illustrates a pulse generator usable in the apparatus of FIG. 5.

FIG. 6 shows the portion of FIG. 5 within the dotted box 60. The letters in FIG. 6 denote corresponding waves of FIG. 7.

In FIG. 6 the frequency of the oscillator 51 is higher than the PRF of the test pulses and is selected to allow convenient division to produce both the test pulse frequency and the duration of the broad initial pulses. It is here selected as 320 kHz. The output of the oscillator is supplied to a binary counter-divider 54 which yields a plurality of outputs 71 for the desired range of test pulse frequencies. One of the outputs of 54 is selected by a multiplexer 72 under the control of inputs a, b, c. An 8:1 multiplexer is here shown, allowing any one of 8 inputs to be delivered to the output line 73. Test pulse frequencies of 5 to 80 kilohertz are presently preferred, but lower and higher frequencies may be employed if desired.

To facilitate illustrating the waveforms, a frequency of 1250 Hertz has been selected. The corresponding frequency in line 73 is 2500 Hertz and is shown at C. This is inverted to form wave D. These waves are supplied to respective flipflops FF1 and FF2 whose function is to divide by 2 and also to establish a 90° relationship between the outputs thereof.

The flipflops may be of commercially available type. As here shown, the positive excursion of the wave to the clock input CL transfers the condition of the D input to the Q output. $\overline{Q}$ is the inverse of Q, and R is a reset terminal. Initially these FFs as well as other FFs in the drawing are reset so that Q is low (0) and $\overline{Q}$ is high (1). The counters are also reset. This is accomplished by the circuit 80 wherein, when the switch is closed, the capacitor starts charging and at a given voltage the output R of the inverter goes low for reset.

FF2 divides input C by 2 to give wave F. The interconnection between FF2 and FF1, together with input D, yields an output E which has the same frequency as F but is delayed by 90° with respect thereto. An output G of divider 54 is supplied to another divider 55, several of whose outputs are supplied to multiplexer 74 so as to allow convenient selection of the initial pulse duration. An output H is here selected as 78 Hertz.

To allow room for subsequent waveforms, wave H is moved to the left by one-half of its cycle, to position H' as shown by the dot-dash lines.

Output H' is supplied directly to NOR 75. It is also supplied to decade counter-divider 76 which produces a pulse J at every tenth pulse of H. In counting, divider 76 maintains its output for the full cycle of H, so that the width of the pulse in J is equal to a full cycle of H. This is inverted to form K, and applied to NOR 75. The NOR circuit functions conventionally to yield a low (0) output whenever any input is high (1), and yields a high (1) output when all of its inputs are low (0). Thus inputs H' and K to NOR 75 give an output L which is high when both H' and L are low.

The interval between successive pulses in J and K is nine times the pulse length due to the divide-by-ten in decade counter 76. This is impractical to illustrate in FIG. 7. The interval, however, is shown at 33 in FIG. 4a.

Wave L is applied to FF3 and FF4 to produce respective outputs M and N which go high on the positive rises of respective waves F and E applied to the clock inputs thereof. Outputs M and N remain high until the positive rises of F and E next following the times at which L goes low. The outputs serve to produce properly timed bursts of quadrature gate and test pulses.

The inverted outputs $\overline{M}$ and $\overline{N}$ are applied to a three-pole triple-throw function switch 77. In the positions shown, $\overline{N}$ is supplied to NOR 78 along with wave E, thereby producing an output V which is the inverse of E but occurs only within the low excursion of $\overline{N}$ corresponding to the high excursion of N as shown. Similarly, wave $\overline{M}$ is supplied to NOR 79 along with wave F, thereby giving an output U which is the inverse of F but occurs only within the low duration of $\overline{M}$ corresponding to the positive duration of M as shown. As will be noted, waves U and V are displaced by 90° at the frequency thereof, thus providing quadrature gate signals for the quadrature detectors 64, 64' of FIG. 5. The signals, upon differentiation, yield short gate pulses at the edges thereof. Appropriate pairs of pulses having a 90° relationship are then used for gating the detectors, in accordance with known principles. In one particular embodiment, differentiated pulses occurring at the position going edges of U and V were used.

Wave $\overline{M}$ is applied to NOR 81 and, together with NOR 82, produces bursts of test pulses in proper time relationship with the broad initial pulse as illustrated in FIG. 4a. Three different duty cycles of the test pulses may be selected by ganged switches 83, 84. In the positions shown, 50% duty cycles are produced. One input to NOR 82 is grounded. Thus the output is $\overline{F}$ and is supplied to NOR 81 along with $\overline{M}$. Accordingly, the output at 85 is the portion of F occurring during the low portion of $\overline{M}$, corresponding to the high portion of M as shown. The resulting burst is shown at T-1. As will be explained hereinafter, the pulse driver utilizes the low (0) portions of the test pulse waveforms to produce corresponding driving pulses. Accordingly the wave at 85 is inverted to produce the output test pulse burst at 86.

For 75% duty cycle pulses, both waves E and F are applied to NOR 82. The output of NOR 82 is then low when both E and F are low. This is inverted by NOR 81 and confined to the low portion of $\overline{M}$. The resulting test pulse burst in line 85 is shown at T-2.

For 25% duty cycle pulses, waves E and F are also applied to NOR 82, but the output is inverted by 87 before being applied to NOR 81. Accordingly the output in line 85 is the inverse of the output for 75% pulses, as shown at T-3.

The broad initial pulse is produced by NOR 88, whose inputs are J, N and M. The output P is low when any of the inputs is high. Accordingly the initial pulse P goes low when J goes high, and stays low until N goes low.

It will be noted that the end of the positive excursion of N occurs slightly after the end of M. Since $\overline{M}$ is used to produce the test pulse burst, the end of the initial pulse P occurs slightly after the last test pulse. Also, the gate pulses U and V are timed so that, by selecting suitable polarities of differentiated pulses produced therefrom, the last gating of the quadrature detectors will occur ahead of the end of the initial pulse. Accordingly any extraneous pulses produced at the end of P will not affect the proper operation of the circuit.

Function switch 77, in its intermediate position B, grounds one input of NOR 78, 79 and 81. Consequently a continuous series of test pulses is produced at output 86 and the gate pulse outputs U and V are continuous. This allows the apparatus to be used for testing non-magnetic materials where composite pulses are unnecessary.

In the calibrate position of switch 77, one input to each of NOR 78 and 79 is grounded so that continuous series of gate pulses are produced. One input to NOR 81 is supplied from a counter divider 89, so that various lengths for the test pulse bursts can be obtained for calibration purposes.

Figure 8:
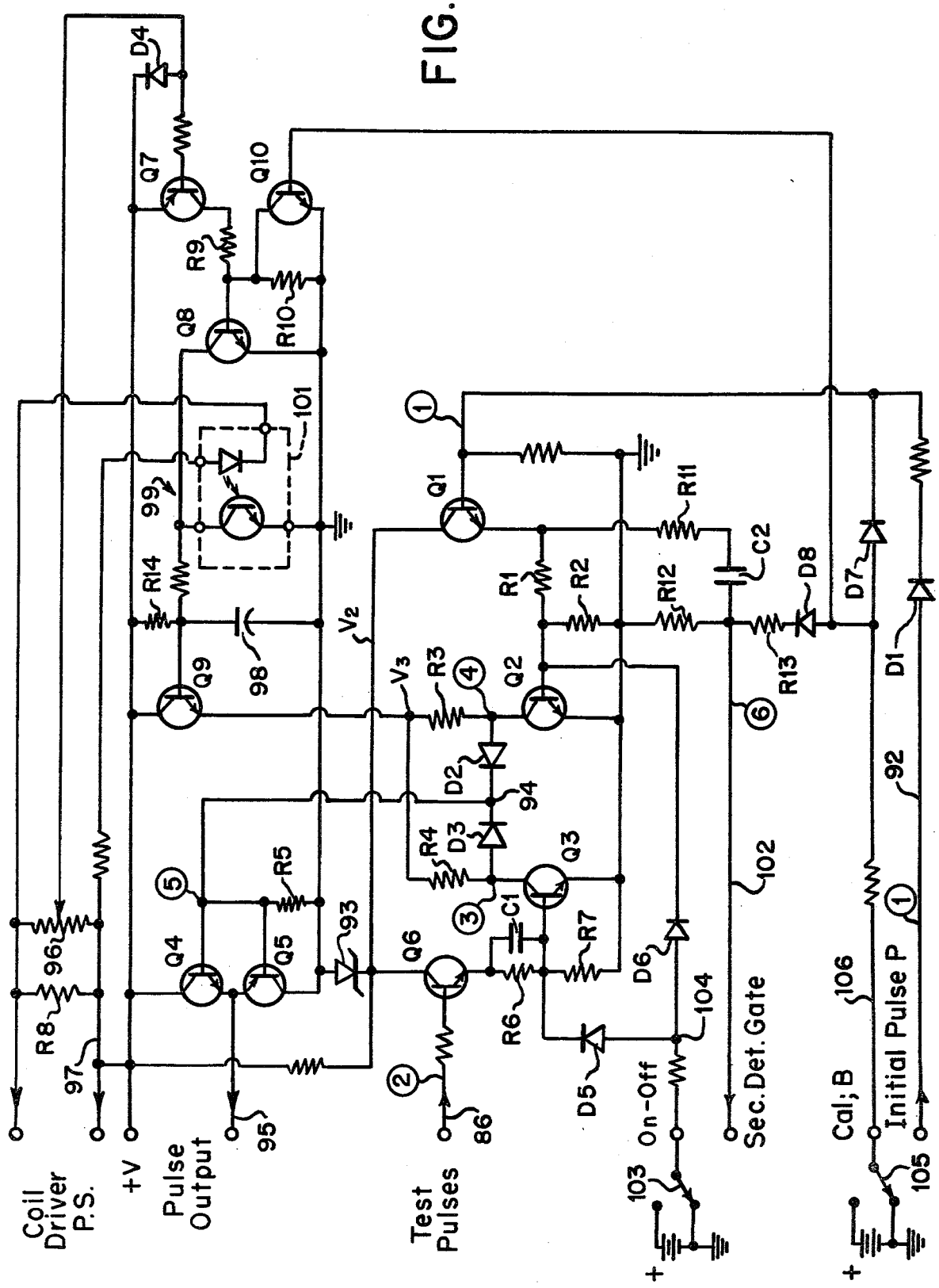
FIG. 8 is a schematic of a pulse driver usable in the apparatus of FIG. 5.
Figure 9:
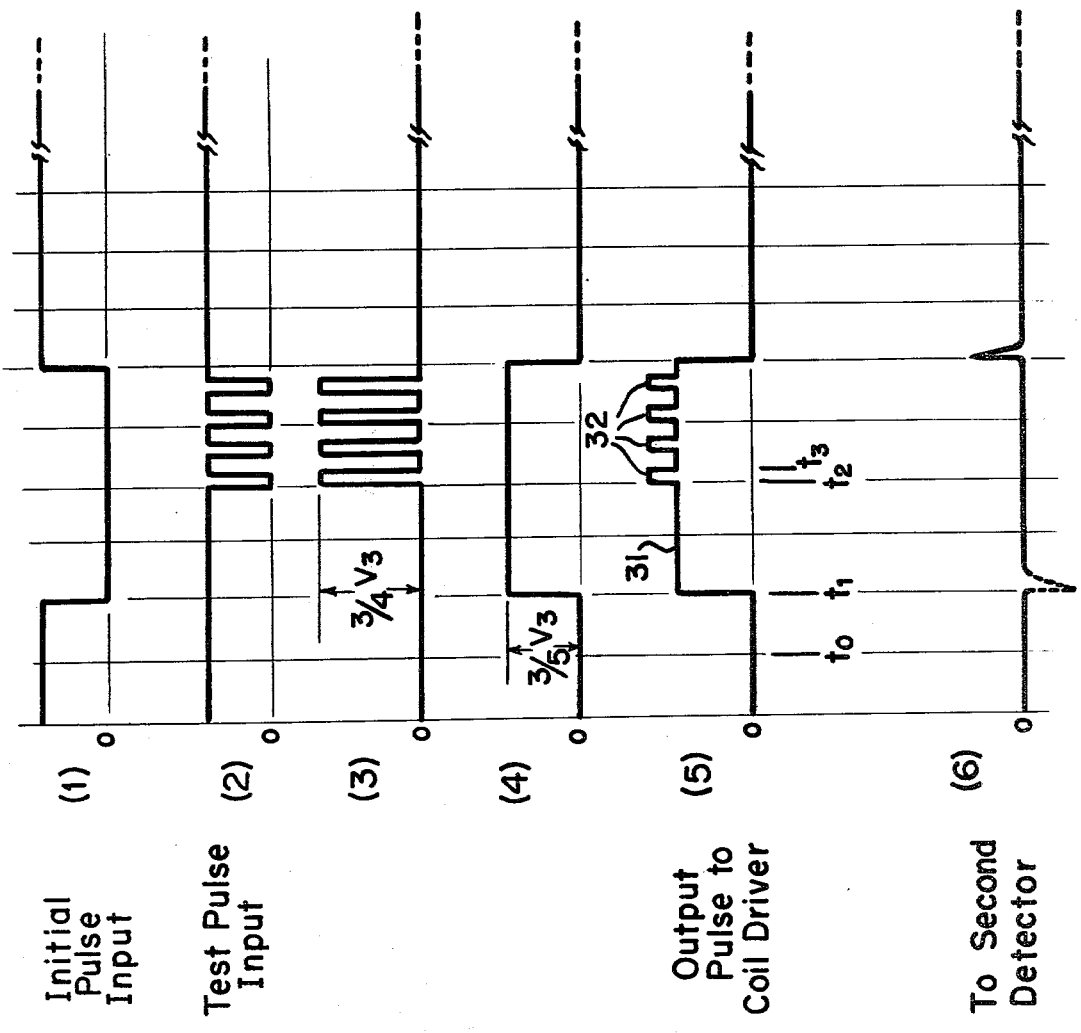
FIG. 9 shows waveforms applicable to FIG. 8.

FIG. 8 shows a circuit for pulse driver 58 and second detector gate generator 67 within the box 91 of FIG. 5. FIG. 9 shows explanatory waveforms which appear at corresponding numbered points in FIG. 8 during normal operation.

Figure 7:
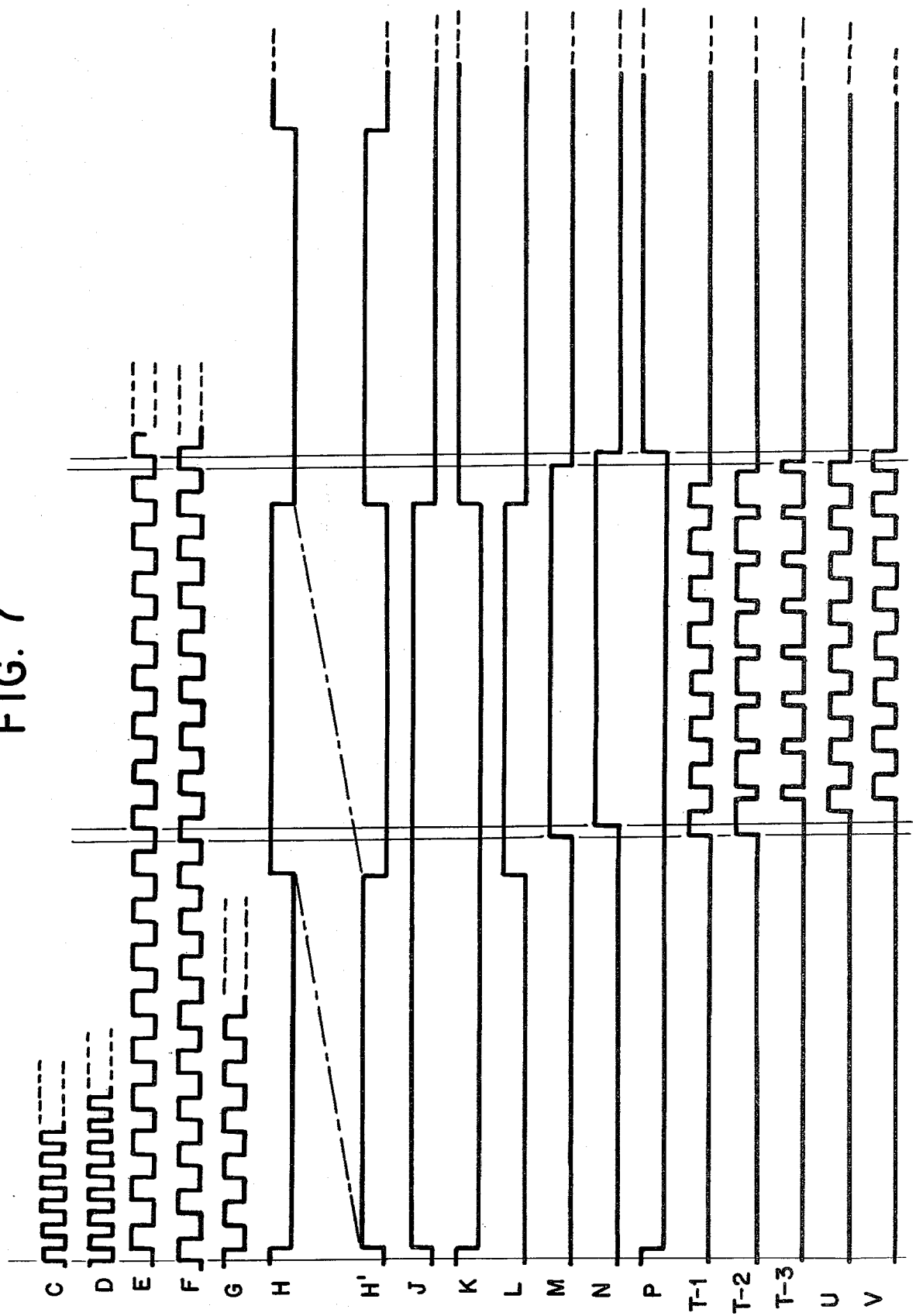
FIG. 7 illustrates waveforms applicable to FIG. 6.

The initial pulse waveform P of FIG. 7 is applied to input line 92, and thence through diode D1 and a resistor to the base of Q1. Q1 functions as an emitter follower and the output voltage is divided by resistors R1, R2 and applied to the base of Q2. Supply voltage V2 is maintained at a desired lower voltage than V by Zener 93.

At time $T_0$ the initial pulse is high, Q1 is on (conducting) and Q2 is on. When the initial pulse goes low at $t_1$ the transistor Q1 is turned off and Q2 is turned off. The voltage V3 is normally supplied from the power line voltage V through Q9 whose function will be described later. Resistor R3 in the collector circuit of Q2 produces a selected amplitude of the initial pulse as shown at 4. This is applied through diode D2 to the bases of transistors Q4, Q5. A voltage division is produced by R3 and R5, and is here selected, for illustrative purposes, as 3/5V3.

The test pulse burst from line 86 of FIG. 6 is applied to the base of Q6 which functions as an emitter follower. A portion of the emitter output, determined by the voltage divider R6, R7, is applied to the base of Q3. Q6 is initially on and Q3 is on. At $t_2$, Q6 and Q3 go off, and thereafter go on and off in accordance with the test pulses.

The collector output of Q3 hence provides a test pulse burst as shown at 3. This is supplied through diode D3 to Q4, Q5, the amplitude being voltage divided by R4 and R5. R4 is made less than R3 and the voltage division for the test pulses is here assumed, for illustrative purposes to be $\frac{3}{4}$V3. While Q2 is off, between $t_1$ and $t_2$, the higher voltage at 94 back-biases D3. However, when Q3 goes off between $t_2$ and $t_3$, the higher voltage of wave 3 passes through D3 to point 94 and back-biases D2. Thereafter the conditions alternate for successive test pulses.

Accordingly, the waveform at the bases of Q4, Q5 is as shown at 5 in FIG. 9. This is the same as the composite pulse shown in FIG. 4a, the amplitude of the superposed test pulses 32 being 25% of the amplitude of the broad pulse 31. The emitter outputs of Q4, Q5 are supplied through line 95 to the coil driver 59 of FIG. 5.

In operation it is desirable to regulate the current in the primary coil 13 of FIG. 5. To this end, resistor R8 is connected in series with a transistor in the coil driver circuit 59 to which the composite pulses in line 95 are applied, thereby providing a voltage proportional to the current in the stage. A desired fraction of this voltage is picked off by potentiometer 96 and supplied to the base of Q7. As will be understood, this voltage will be below the power supply voltage of line 97. Diode D4 provides protection against possible polarity reversal. The output voltage of Q7 is divided by R9, R10 and applied to the base of Q8. The collector output of Q8 is supplied to the base of Q9. In normal operation Q7, Q8 and Q9 will all be conducting, and the conductance of Q9 will be controlled by the voltage picked off by potentiometer 96. This maintains voltage V3 at the desired value. A large capacitor 98 shunts the base of Q9 so that the conductance is constant from pulse to pulse, but varies with the average current supplied to the driver stage.

As a safety factor, the maximum current through the coil driver stage is limited by circuit 99, to avoid accidental damage. The circuit here takes the form of an optical isolator 101, of commercial type. Broadly, a light emitting diode controls a photosensitive transistor. The diode responds to the voltage drop across R8. If the voltage is too high, the transistor conducts to reduce the input to Q9, thereby reducing V3 and thus the amplitude of the composite pulse in line 95.

Gate pulses for the second detectors 66, 66' of FIG. 5 are also developed in FIG. 8. To this end the emitter output of Q1 is supplied through R11 to capacitor C2, and the latter is returned to ground through R12. When the initial pulse 1 goes high at the end thereof, Q1 conducts to produce a positive-going pulse in line 102, as shown by wave 6. Thereafter C2 charges through R11, R12, the time constant being selected to provide a sufficiently long trigger pulse for actuating the second detectors. When the next initial pulse arrives, a negative differentiated pulse will be produced as shown dotted in 6, but this is ineffective to actuate the second detectors.

It is advantageous to apply power to the probe coil 13 in FIG. 2 only when measurements are actually being made, so as to avoid unnecessary heating. Accordingly a switch 103 is provided which applies a positive voltage to point 104, thereby turning transistors Q2 and Q3 on through diodes D5 and D6. This prevents the transistors from developing the respective components of the composite output pulse. Switch 103 may be foot-actuated if desired.

During calibration and in position B of function switch 77 in FIG. 6, continuous test pulses are supplied from the line 86 to Q6, so that a continuous series of test pulses is produced by Q3 and supplied to the output line 95. Q1 and Q2 are disabled by actuating switch 105 so as to apply a positive voltage to line 106. This acts through diode D7 to turn on Q1 and therefore Q2. Also, the positive voltage in line 106 is supplied through D8 and R13 to line 102, thereby maintaining line 102 high and keeping the second detectors continuously open to pass quadrature signals. In addition, the positive voltage of line 106 is supplied to the base of Q10, thereby turning Q10 on and short-circuiting the input of Q8. Hence the regulating circuit is inoperative and Q9 is at its maximum conductance as established by R14.

Figure 10:
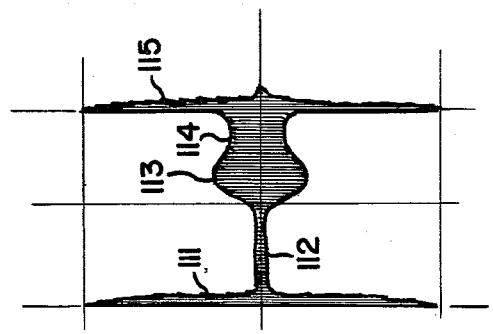
FIG. 10 illustrates a CRT representation of the output of the tuned amplifier of FIG. 5.

FIG. 10 illustrates a CRT oscilloscope representation of the output of amplifier 62 (FIG. 5) under normal operating conditions. The oscilloscope is synchronized with the composite pulses. After an initial transient at 111, the output remains approximately zero for the first half of the composite pulse (FIG. 4a) as indicated at 112. At the beginning of the burst of test pulses, the output rises at 113, and thereafter falls to a stable value at 114. This is followed by another transient period 115 at the end of the pulse. As above explained, the second detectors gate the outputs of the quadrature detectors to the succeeding circuits at the end of the stable period 114.

The second detectors could be gated somewhat earlier in the stable region 114. However, a different choice of test pulse PRF and initial pulse duration may shorten the stable region so that gating at the end thereof is preferred. Later gating of the second detectors is possible, if the quadrature detectors hold their final outputs as is the case in sample-and-hold detectors.

It will be understood that portions 113 and 114 represent the output of the null coils 18, 18' after amplification and filtering by the tuned circuit of amplifier 62. In FIG. 10, the oscilloscope gain is very high, so that a very small unbalance of the null coils is exhibited. When flaws occur, the amplitudes of regions 113, 114 change from burst to burst, and the changes are detected by the subsequent quadrature detectors.

In operation, it is important to know that the material under test is being saturated. For some applications it may be possible to determine in advance the current required for saturation. For example, if a sample of the tube to be tested is available, a flaw of known size may be formed therein, such as a reference notch. This should be formed in such a way as to avoid any changes in permeability of the material due to the formation of the notch. If the tube is then tested, a certain noise level will show up in the indicating circuits due to random variations in permeability. The amplitude of the composite pulses may then be increased until a notch signal of sufficient amplitude is obtained, say twice the noise level. Having ascertained the necessary current level by this test, similar levels can be employed in an actual field test. While useful for some applications, such a test may not suffice in practice since the exact composition of the tubes to be tested may not be known, or an identical sample may not be available.

Accordingly, the present invention provides means for indicating when the material under test is being driven into the saturation region.

Referring to FIG. 5, the output of one null coil 18 is supplied to a C-R differentiating circuit 121 and thence through amplifier 122 to oscilloscope 123. As the material is driven into saturation, distortion products occur in the signal picked up by coil 18. These distortion products are emphasized by the differentiating circuit.

Figure 11:
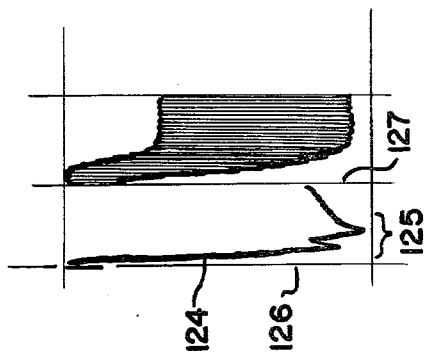
FIG. 11 is a CRT representation of the differentiated output of a single pick-up coil.

FIG. 11 indicates at 124 the type of waveform which may be observed on oscilloscope 123. A signal 125 is produced by the distortion components occurring as the material is driven into saturation. Line 126 corresponds to the beginning of the composite wave of FIG. 4a, and line 127 corresponds to the end of the initial flat portion and the beginning of the test pulses. For a given pulse current, more readily magnetizable materials will yield indications 125 occurring earlier in the waveform, that is, toward the left line 126. For materials which are more difficult to saturate, the indication 125 will move to the right. Similarly, in tubes of the same material but having different wall thicknesses, as the wall thickness decreases the indications 125 will move to the left, and as the wall thickness increases the indications will move to the right. Accordingly, the indications may be used to select an operating current level which will provide reasonable assurance that the material is being driven into saturation.

The portion to the right of line 127 indicates the initial transient conditions during a burst of test pulses, followed by a relatively stable level. This of course is for one pickup coil, so that the nulling effect of the other coil is not present.

It is difficult to correlate the details of the signal 124, 125 with the state of the magnetic material under test, since changes in normal and incremental permeability, inductance of the coils as affected by changes in permeability, and magnitudes of the DC and AC components of the pulses are involved, along with perhaps other factors. Also the precise effect of the differentiation, taking into account the foregoing factors, is difficult to ascertain. Considerable variation in the amplitude and shape of the wave has also been noted with different current levels, and with different probes and materials under test. Therefore an adequate explanation for the results obtained are not known at the present time. However, it is presently believed that the indication is useful in practice.

The foregoing discussion of the specific embodiment is primarily with respect to composite pulses as shown in FIG. 4a. If operation in accordance with FIG. 4b is desired, the pulse driver circuits of FIG. 8 may be suitably modified or different circuits developed for the purpose. For example, Q3 may be rearranged so as to normally short-circuit a portion of R3, the short-circuit being removed during the test pulse, thereby changing the divider action of R3 and R5. Or, similarly, a portion or R5 may be short-circuited by Q3 during the test pulse occurrence.

If operation is desired in accordance with FIG. 4c the pulse generator of FIG. 6 may be changed to produce the test pulse burst immediately following the initial pulse, and resistors R3 and R4 in FIG. 8 made equal. Or, a composite burst like FIG. 4c could be produced in FIG. 6, and applied to either pulse input of FIG. 8.

It is preferred to employ DC pulses to form the composite pulses of FIG. 4, as shown. However, it is possible to use sinusoidal variations to provide the AC component for inducing eddy currents in the object, instead of the test pulse bursts shown. FIG. 12 shows an example. Here the sine wave 131 is formed on the top of the broad pulse 132. With such composite pulses, quadrature detection and the second detector may still be employed.

Although it is preferred to employ composite pulses, for some applications simpler DC pulse arrangements may be usable, particularly for materials which are readily saturated.

FIG. 13 illustrates the use of bursts of pulses 133, 133' separated by a comparatively long time interval 134. As before explained, the DC pulses will have a DC component such as indicated by dotted line 135. For a 50% duty cycle, the DC level will be one-half the peak value. For 75% duty cycle pulses, the DC level will be higher, and for 25% duty cycle it will be lower. Since the coil to which the pulses are applied will have inductance current will build up during each pulse, and decay somewhat therebetween, yielding an overall DC or unidirectional current. In some instances the DC level and the duration of a given pulse burst may be sufficient to saturate the magnetic material, thereby enabling satisfactory flaw detection. Quadrature detection may be employed. Also, a second detector may be gated at or near the end of a pulse burst, so as to produce an indication when the saturation is most complete and the preceding circuits have reached a comparatively stable condition.

In some instances, with easily saturated material, it may be possible to employ a continuous series of DC pulses without excessive heating, as illustrated in FIG. 14. Here the duty cycle may be selected to yield an adequate DC level, such as indicated by line 136. Quadrature detection may still be employed.

Figure 15:
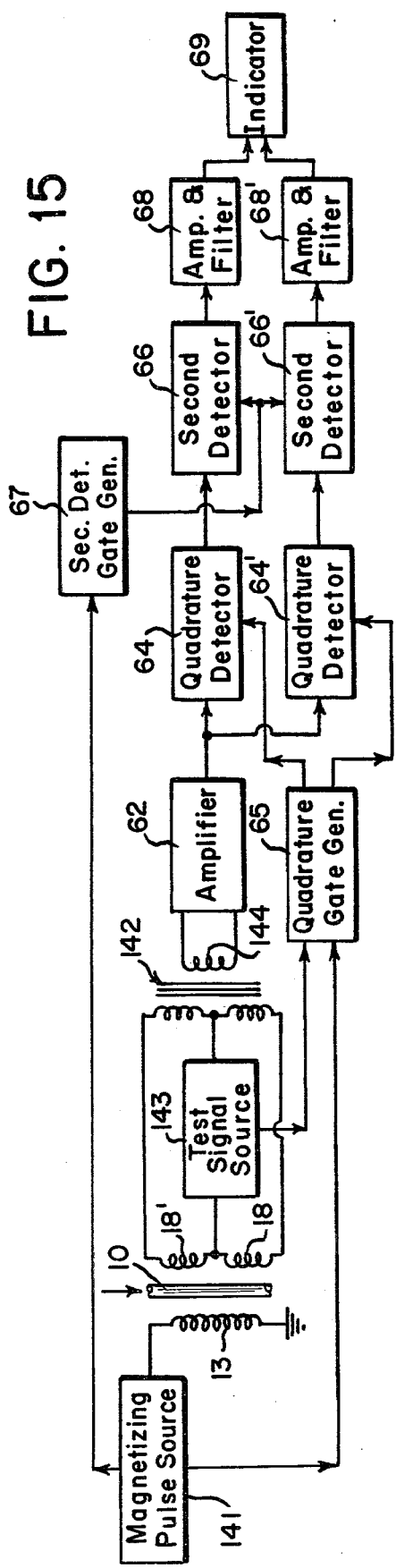
FIG. 15 is a block diagram of a modified flaw detector using a bridge configuration.

Referring to FIG. 15, a modification of the flaw detector of FIG. 5 is shown. Here only DC magnetizing pulses from a source 141 are applied to the primary coil 13 of the probe assembly of FIG. 2. The pulses may be produced in the manner of wave 4 in FIGS. 8 and 9. The detector or pickup coils 18, 18' of the probe are here connected in a bridge configuration with the center-tapped primary of transformer 142. The test signal from source 143, having an AC component, is applied across one diagonal of the bridge. The test signal may be intermittent bursts of pulses occurring during the latter half of respective magnetizing pulses similar to FIGS. 4a and 4b and may be developed in the manner of wave 3 in FIGS. 8, 9, or immediately after the saturation pulses similar to FIG. 4c. With DC test pulses, the DC component thereof will aid in preserving sufficient saturation of the object under test, as discussed before. However, short bursts of sinusoidal waves may be employed if desired, similar to wave 131 in FIG. 12. Small amplitudes of the AC component may suffice, and aid in reducing the incremental permeability of object 10, as previously described.

Coils 18, 18' are advantageously connected in a series opposition or null configuration so that voltages induced therein by primary coil 13 will cancel. Balancing circuits may be employed in accordance with conventional practice to initially balance the bridge. The AC component of the test signal in coil 18, 18' will induce eddy currents in object 10 and variations in the eddy currents due to flaws, etc. will unbalance the bridge and produce a signal in the output winding 144 of the transformer. This signal is amplified, quadrature detected, gated by second detectors, and processed and indicated as described in connection with FIG. 5.

The gating in 66, 66' should be sufficiently delayed with respect to the initiations of the DC magnetizing pulses so that the resultant signals will correspond to sufficient saturation of the object. If the test signal occurs only during or immediately after a DC pulse, the gating should also be delayed with respect to the successive initiations of the test signal so as to eliminate transient conditions and provide outputs corresponding to stable values. With the detection and gating, it is possible to use a continuous series of short DC pulses or a continuous sine wave for the test signal provided overheating is avoided, since the gating can eliminate the effects of the test signal between DC magnetizing pulses and during the initial portion of each DC magnetizing pulse, so that the resultant detected signals will correspond to sufficient saturation of the object. In general, the gating is at intervals delayed with respect to the respective initiations of the DC magnetizing pulses and AC components occurring during or immediately after the DC pulses.

Differentiation of the output of one of coils 18,18' to indicate saturation, as described in connection with FIGS. 5, 10 and 11, may be employed if desired.

Figure 16:
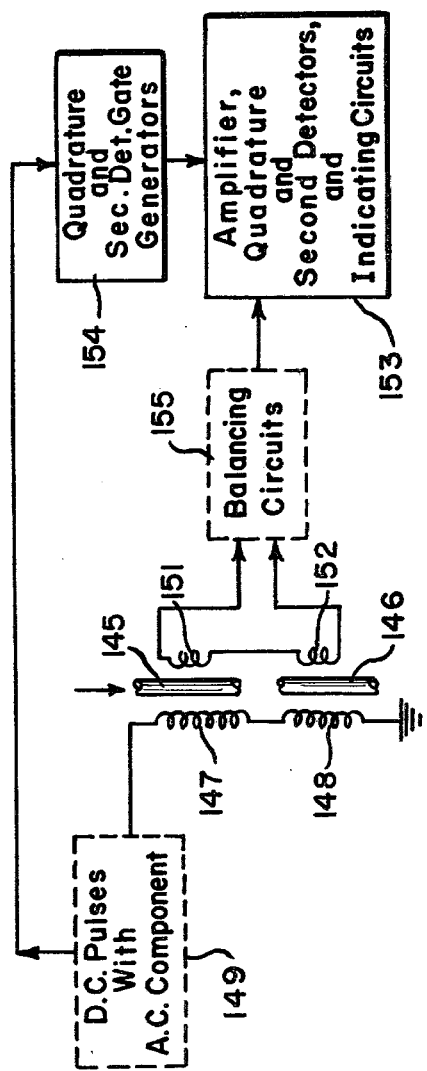
FIG. 16 illustrates a comparatory type apparatus using composite pulse driving.

FIG. 16 shows a comparator for comparing an object 145 under test with a reference object 146. The object 145 under test is placed in or moved with respect to a test coil arrangement comprising primary coil 147 and secondary or pickup coil 151. A reference coil arrangement with a primary coil 148 and secondary coil 152 is provided for the reference object 146. The coils may be internal or external to the objects, as required. Such apparatus is useful to determine variations in size, material, etc. of an object.

Composite signals containing DC magnetizing pulses and an AC component are supplied to the primary coils 147, 148 from source 149, similar to those used in the flaw detector of FIG. 5. The outputs of secondary coils 151, 152, advantageously connected in opposition to form a null configuration, are supplied to amplifier, quadrature and second detectors, and indicating circuits in block 153, which may be similar to FIG. 5. Quadrature and second detector gates are generated in 154 under the control of signals from 149 and supplied to 153. Balancing circuits 155 may be employed if desired, in accordance with known practices. Differentiating of the output of one of coils 151, 152 to indicate saturation may be employed, as described above.

With quadrature detection and gating, resultant signals can be produced which correspond to sufficient saturation of the object under test to reduce the permeability to a small value, and transient conditions are eliminated so that the signals correspond to stable values.

Figure 17:
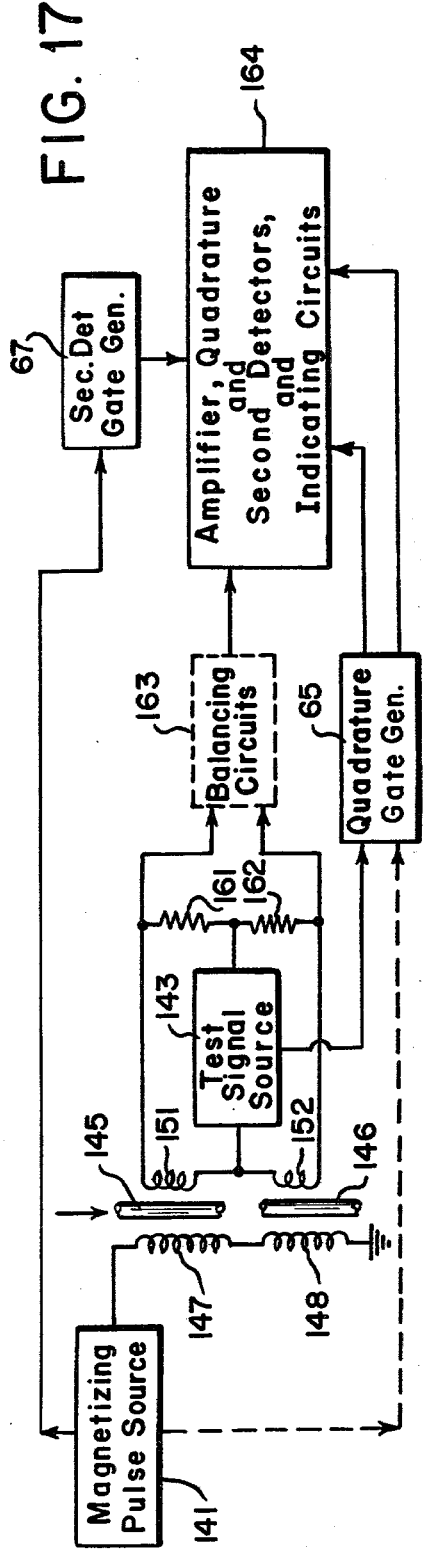
FIG. 17 illustrates a modified comparator type apparatus using a bridge configuration.

FIG. 17 shows a comparator using a bridge arrangement similar to FIG. 15. Here DC magnetizing pulses from a source 141 are applied to the primary coils 147, 148. Test signals from source 143 are applied across the diagonal of a bridge formed by coils 151, 152 and resistors 161, 162. The signal across the other diagonal of the bridge is fed through balancing circuits 163 (if required) to amplifying, quadrature detecting, gating and indicating circuits 164. Quadrature and second detector gate signals may be generated in 65, 67 similar to those described above.

Resistance legs 161, 162 are here shown in the bridge circuit instead of a center-tapped transformer, and other bridge arrangements may be employed as known in the art.

Figure 18:
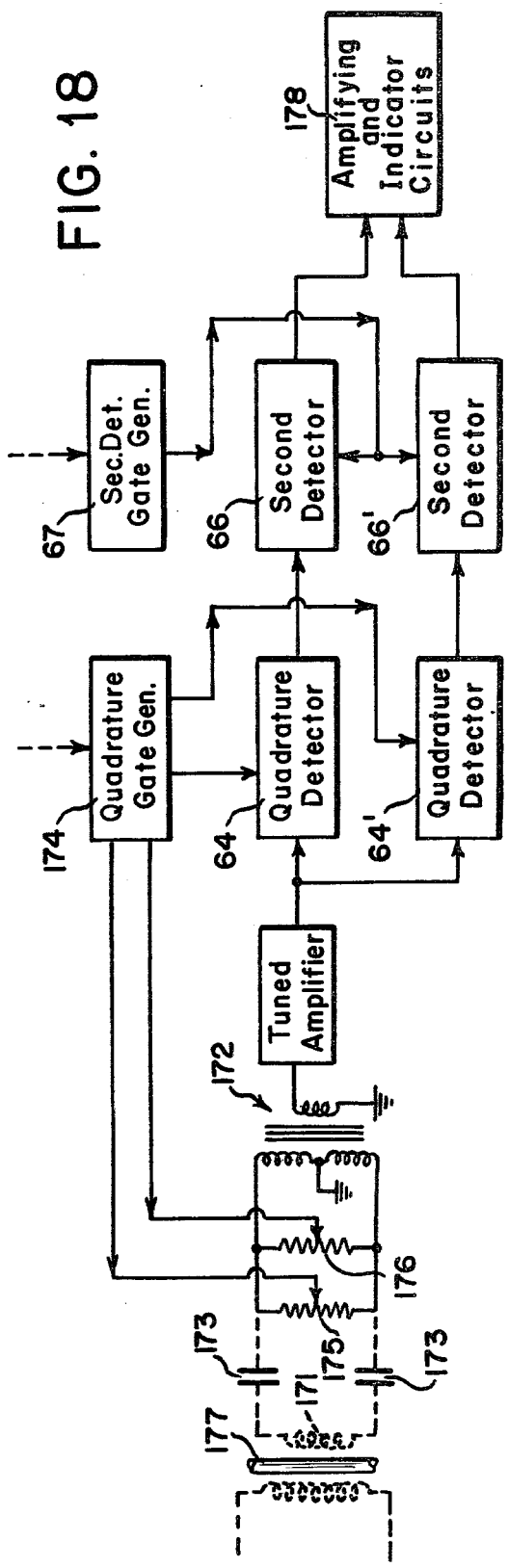
FIG. 18 illustrates a comparator type apparatus with an electrically generated reference signal.

FIG. 18 illustrates an arrangement in which an electrical balancing signal is produced and a reference object in a test coil is used as a basis of comparison for subsequent objects to be tested. Here coil 171 may be one of the coils 18,18' of the flaw detector of FIG. 5 or 15, or the test coil 151 of a comparator such as shown in FIG. 16 or 17. Coil 171 is connected to a center-tapped transformer 172 through capacitors 173 which provide DC isolation. If the circuit unduly loads coil 171, an isolating amplifier may be employed.

Quadrature gates from generator 174 are applied to the sliders of potentiometers 175, 176 connected across the center-tapered primary of transformer 172. The secondary of the transformer is connected to an amplifier, quadrature detectors, second detectors, and amplifying and indicating circuits similar to those described above.

Object 177 is initially a reference object and potentiometers 175, 176 are adjusted to yield a reference indication in 178. Then the reference object is removed and objects to be tested are inserted. Variations in a test object from the reference are indicated by departures from the reference indication in 178. Advantageously the initial adjustment produces a balance which yields a zero reference indication, so that small variations of test objects from the initial reference object can be indicated, as well as the direction of the variation.

The invention has been described in connection with presently preferred embodiments thereof including preferred forms of driving pulses. Other forms of driving signals, although not preferred, may be usable under some conditions. Other features have also been described which promote the overall effectiveness in determining flaws or defects in objects of magnetic material, and especially tubes. It will be understood that modifications of the specific embodiments may be made within the spirit and scope of the invention, and that certain features of the invention may be employed and others omitted, as meets the requirements of a particular application.

We claim:
1. Apparatus for the eddy current testing of objects of magnetic material for variations therein which comprises
    (a) a test head including coil means adapted to be magnetically coupled with a said object to be tested,
    (b) means for applying to said coil means intermittent DC voltage pulses for producing magnetic flux in the object and a voltage having a substantial AC component for inducing eddy currents therein,
    (c) said AC component occurring at least during respective DC pulses and having a period which is short compared to the duration of a said pulse,
    (d) means connected with said coil means for producing a signal corresponding to variations in said eddy currents,
    (e) quadrature detecting and gating means for producing quadrature detected signals from said signal at predetermined gated intervals prior to or at the ends of said DC pulses respectively and delayed with respect to the respective initiations of said DC pulses and AC components occurring during the DC pulses,
    (f) said quadrature detected signals being produced at quadrature-related points synchronized with said applied AC component and the delay of said intervals being at least a plurality of periods of said AC component,
    (g) and means responsive to said detected signals for indicating variations in said object.

2. Apparatus according to claim 1 in which said DC voltage pulses have a DC component sufficient to drive said object into the saturation region thereof wherein the permeability thereof is small compared to the maximum permeability thereof.

3. Apparatus according to claim 1 in which said coil means of the test head comprises a primary coil to which said DC pulses are applied and a pair of detector coils for producing said signal corresponding to variations in said eddy currents.

4. Apparatus according to claim 3 in which said pair of detector coils are connected in null configuration, and said DC pulses and said voltage having an AC component are applied to said primary coil.

5. Apparatus according to claim 3 in which said DC voltage pulses are applied to said primary coil, said detector coils are connected in a balanced bridge circuit, and said voltage having an AC component is supplied to the detector coils.

6. Apparatus according to claim 3 including means for differentiating the output of one of said detector coils, and means for indicating the differentiated output.

7. Apparatus for the eddy current testing of objects of magnetic material for variations therein which comprises driving means for intermittently producing in said object unidirectional flux for decreasing the permeability thereof and AC flux for producing eddy currents therein, sensing means for producing an auxiliary output varying with said unidirectional flux and a test output varying with said eddy currents, means for differentiating said auxiliary output and indicating the differentiated output, and means responsive to said test output for producing indications of variations in said object.

8. Apparatus for the eddy current testing of objects of magnetic material for variations therein which comprises
   (a) a test head including coil means adapted to be magnetically coupled with a said object to be tested,
   (b) means for applying to said coil means intermittent DC voltage pulses for producing magnetic flux in the object and a voltage having a substantial AC component for inducing eddy currents therein,
   (c) said AC component occurring at least during or immediately after the respective DC pulse and having a period which is short compared to the duration of the pulse,
   (d) circuit means connected with said coil means for producing a test signal corresponding to variations in said eddy currents,
   (e) means responsive to said test signal for producing indications of variations in said object,
   (f) and a differentiating circuit supplied with signals from said coil means corresponding to variations in the magnetic flux in the object during said DC pulses respectively,
   (g) and means for indicating the output of said differentiating circuit.

9. Apparatus for the eddy current testing of objects of magnetic material for variations therein which comprises
   (a) a test head including coil means adapted to be magnetically coupled with a said object to be tested,
   (b) means for applying to said coil means intermittent DC voltage pulses for producing magnetic flux in the object and a voltage having a substantial AC component for inducing eddy currents therein,
   (c) said AC component occurring when magnetic flux is produced in the object by the respective DC pulse, said AC component having a period which is short compared to the duration of the pulse,
   (d) means connected with said coil means for producing a signal corresponding to variations in said eddy currents,
   (e) a pair of quardature detectors for producing quadrature component signals from said signal at quadrature-related points synchronized with said applied AC component,
   (f) a pair of second detectors and gating means for receiving said quadrature component signals and producing quadrature detected signals at intervals delayed with respect to the respective initiations of said DC pulses and AC components,
   (g) the delay of said intervals being at least a plurality of periods of said AC component,
   (h) and means responsive to said detected signals for indicating variations in said object.

10. Apparatus for the eddy current testing of magnetic material for variations therein comprising:
   (a) a test head including a primary coil for producing magnetic flux in an object under test;
   (b) means for generating and supplying to the test head primary coil periodic D-C pulses having a duty cycle on-period of sufficient magnitude and time duration producing sufficient magnetic flux to periodically drive the test object into a transient stabilized magnetic saturation region of reduced permeability;
   (c) said periodic D-C pulses having a cyclic amplitude varying component forming an A-C component having sufficient time duration to induce an interval of transient stabilized eddy currents in the test object during a time interval of said transient stabilized magnetic saturation;
   (d) said test head including pick-up coil means separate from said primary coil and responsive to induced eddy currents in the test object;
   (e) amplifying and detecting means supplied with the output of said pick-up coil for producing test signals corresponding to sensed eddy current variations only during the periodic intervals in which both magnetic saturation and induced eddy current flow are transient stabilized; and
   (f) indicating means responsive to said test signals.

11. Apparatus according to claim 10, in which said DC pulses applied to the primary coil are intermittent composite DC pulses each having a relatively broad DC component and an AC component having a period which is short compared to the duration of the composite pulse.

12. Apparatus according to claim 10, in which said DC pulses applied to the primary coil are intermittent composite DC pulses each having a relatively broad initial value followed by a plurality of substantially shorter DC pulses.

13. Apparatus according to claim 12, in which the peak values of said shorter DC pulses are approximately equal to or greater than said initial value and the minimum values of the shorter pulses are greater than the minimum value of the composite pulse.

14. Apparatus for the eddy current testing of objects of magnetic material for variations therein which comprises
   (a) a test head including a primary coil for producing magnetic flux in a said object,
   (b) means for applying to said primary coil intermittent composite DC pulses each having a relatively broad DC component sufficient to drive said object into the saturation region thereof wherein the permeability thereof is small compared to the maximum permeability thereof,
   (c) said DC pulses having an AC component for inducing eddy currents in the object, the AC component having a period which is short compared to the duration of the composite pulse,
   (d) said test head including pickup coil means for sensing variations in said eddy currents,
   (e) amplifying and detecting means supplied with the output of said pickup coil means for producing signals corresponding to variations in the object, said means including a differentiating circuit supplied with signals from the pickup coil corresponding to variations in the magnetic flux in the object during said DC pulses,
   (f) and means for indicating the output of the detector and said differentiating circuit.

15. Apparatus for the eddy current testing of tubes of magnetic material for flaws or defects therein which comprises:
   (a) a probe for insertion into a said tube having a core of magnetic material and a primary coil wound therearound for producing magnetic flux in the tube wall,
   (b) means for intermittently applying to said primary coil composite DC pulses each having a relatively broad DC component for producing magnetic flux in the tube wall and an AC component having a period which is short compared to the duration of the composite pulse for inducing eddy currents in the tube wall, (c) a pair of null coils in said proble for sensing variations in said eddy currents, and (d) circuit means supplied with the output of said null coils for indicating flaws or defects in the tube wall, said circuit means including a tuned amplifier supplied with the output of said null coils, a pair of quadrature detectors supplied from the output of said amplifier, and a pair of second detectors supplied from respective quadrature detectors and gated to pass quadrature signals produced at intervals delayed with respect to the respective initiations of said AC components.

16. Apparatus according to claim 15, in which said second detectors are gated at or near the ends of respective AC components.

17. Apparatus for the eddy current testing of tubes of magnetic material for flaws or defects therein which comprises:

(a) a probe for insertion into a said tube having a core of magnetic material and a primary coil wound therearound for producing magnetic flux in the tube wall, (b) means for intermittently applying to said primary coil composite DC pulses each having a relatively broad DC pulse for producing magnetic flux in the tube wall and an AC component having a period which is short compared to the duration of the composite pulse for inducing eddy currents in the tube wall, said AC component comprising a series of DC pulses shorter in duration than the broad DC pulse, (c) a pair of null coils in said proble for sensing variations in said eddy currents, and (d) circuit means supplied with the output of said null coils for indicating flaws or defects in the tube wall, said circuit means including a tuned amplifier supplied with the output of said null coils, a pair of quadrature detectors supplied from the output of said amplifier, and a pair of second detectors supplied from respective quadrature detectors and gated to pass quadrature signals at or near the ends of respective series of shorter DC pulses.

18. Apparatus for the eddy current testing of tubes of magnetic material for flaws or defects therein which comprises:

(a) a probe for insertion into a said tube having a core of magnetic material and a primary coil wound therearound for producing magnetic flux in the tube wall, (b) means for intermittently applying to said primary coil composite DC pulses each having a relatively broad DC component for producing magnetic flux in the tube wall and an AC component having a period which is short compared to the duration of the composite pulse for inducing eddy currents in the tube wall, (c) a pair of null coils in said probe for sensing variations in said eddy currents, and (d) circuit means supplied with the output of said null coils for indicating flaws or defects in the tube wall, said circuit means including means for differentiating the output of one of said null coils, and means for indicating the differentiated output.

19. Apparatus for the eddy current testing of tubes of magnetic material for flaws or defects therein which comprises:

(a) a proble for insertion into a said tube having a core of magnetic material and a primary coil wound therearound for producing magnetic flux in the tube wall, (b) means for intermittently applying to said primary coil composite DC pulses each having a relatively braod initial value for producing magnetic flux in the tube wall and an AC component having a period which is short compared to the duration of the composite pulse for inducing eddy currents in the tube wall, said AC component comprising a pluraity of DC pulses substantially shorter in duration than the broad initial component of the composite DC pulse, (c) a pair of null coils in said probe for sensing variations in said eddy currents, and (d) circuit means supplied with the output of said null coils for indicating flaws or defects in the tube wall, said circuit means including means for differentiating the output of one of said null coils, and means for indicating the differentiated output.

* * * * *

UNITED STATES PATENT AND TRADEMARK OFFICE
CERTIFICATE OF CORRECTION

PATENT NO. : 4,188,577
DATED : Feb. 12, 1980
INVENTOR(S) : Girish P. Mhatre & Robert A. Brooks It is certified that error appears in the above-identified patent and that said Letters Patent are hereby corrected as shown below:

Col. 3, line 46, "having" should read --have--.
Col. 4, line 18, "comparatory" should read --comparator--.
Col. 5, line 24, "meabiliy" should read --meability--;
        line 34, "thereon" should read --thereof--;
        line 58, "dented" should read --denoted--.
Col. 7, line 68, "They" should read --These--.
Col. 8, line 59, "L" should read "K".
Col. 13, line 19, "or" should read "of".
Col. 15, line 43, "center-tapered" should read --center-tapped--.
Col. 19, line 3, "proble" should read --probe--;
        line 36, "proble" should read --probe--.
Col. 20, line 25, "proble" should read --probe--;
        line 31, "braod" should read --broad--;
        line 36, "pluraity" should read --plurality--.

Signed and Sealed this

Fifth Day of August 1980

[SEAL]

Attest:

SIDNEY A. DIAMOND

Attesting Officer   Commissioner of Patents and Trademarks